(12) United States Patent
Viala et al.

(10) Patent No.: US 9,687,436 B2
(45) Date of Patent: Jun. 27, 2017

(54) PLASTICIZERS FOR NAIL VARNISH

(71) Applicant: COVESTRO DEUTSCHLAND AG, Leverkusen (DE)

(72) Inventors: Sophie Viala, Cologne (DE); Sebastian Dorr, Dusseldorf (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/917,072

(22) PCT Filed: Sep. 19, 2014

(86) PCT No.: PCT/EP2014/070015
§ 371 (c)(1),
(2) Date: Mar. 7, 2016

(87) PCT Pub. No.: WO2015/022438
PCT Pub. Date: Feb. 19, 2015

(65) Prior Publication Data
US 2016/0213596 A1   Jul. 28, 2016

(30) Foreign Application Priority Data
Sep. 23, 2013 (EP) .................................... 13185609

(51) Int. Cl.
*A61Q 3/02* (2006.01)
*A61K 8/85* (2006.01)
*A61K 8/73* (2006.01)
*A61K 8/86* (2006.01)
*A61K 8/37* (2006.01)
*A61K 8/49* (2006.01)

(52) U.S. Cl.
CPC .................. *A61K 8/85* (2013.01); *A61K 8/37* (2013.01); *A61K 8/4973* (2013.01); *A61K 8/731* (2013.01); *A61K 8/86* (2013.01); *A61Q 3/02* (2013.01); *A61K 2800/594* (2013.01)

(58) Field of Classification Search
CPC . A61K 8/85; A61K 8/731; A61K 8/86; A61K 8/37; A61K 8/4973; A61K 2800/594; A61Q 3/02
See application file for complete search history.

(56) References Cited

U.S. PATENT DOCUMENTS

| | | |
|---|---|---|
| 3,117,102 A | 1/1964 | Crowe |
| 3,640,967 A | 2/1972 | Konig |
| 4,626,428 A | 12/1986 | Weisburg et al. |
| 4,808,691 A | 2/1989 | Konig |
| 5,227,155 A | 7/1993 | Castrogiovanni et al. |
| 5,807,540 A | 9/1998 | Junino |
| 2007/0243149 A1 | 10/2007 | Hofacker |
| 2008/0021154 A1 | 1/2008 | Haider et al. |
| 2010/0158835 A1 | 6/2010 | Bandres et al. |

FOREIGN PATENT DOCUMENTS

| | | |
|---|---|---|
| DE | 1770245 A1 | 10/1971 |
| DE | 2650533 A1 | 5/1978 |
| EP | 0292772 A2 | 11/1988 |
| EP | 2046861 A1 | 4/2009 |
| KR | 101044853 B1 | 6/2011 |
| WO | 0054732 A1 | 9/2000 |
| WO | 03094870 A1 | 11/2003 |

*Primary Examiner* — Nannette Holloman
(74) *Attorney, Agent, or Firm* — John E. Mrozinski, Jr.

(57) ABSTRACT

The present invention relates to a nail varnish composition which contains a plasticizer A) and a film-forming agent B), characterized in that the plasticizer A) comprises at least two carbonate structural units of formula (I) and has an average molecular weight of ≥450 g/mol, determined by gel permeation chromatography against a polystyrene standard in tetrahydrofurane at 23° according to DIN 55672-1, and a hydroxyl functionality of ≥1.5 and ≤6.

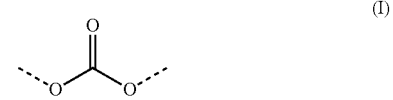

(I)

The invention further relates to a coating which can be obtained from the nail varnish composition according to the invention, to a substrate coated with such a coating, and to a cosmetic method for coating finger and/or toe nails, according to which method a nail varnish composition according to the invention is applied to finger and/or toe nails. The invention also relates to the use of compounds as plasticizers in nail varnish compositions which compounds contain specific carbonate structural units.

13 Claims, No Drawings

PLASTICIZERS FOR NAIL VARNISH

FIELD OF THE INVENTION

The present invention relates to a nail varnish composition comprising a plasticizer A) containing carbonate structural units and a film former B). Further subjects of the invention are a coating obtainable from the nail varnish composition according to the invention, a substrate coated with such a coating according to the invention, and a cosmetic method for coating fingernails and/or toenails, in which a nail varnish composition according to the invention is applied to fingernails and/or toenails. Furthermore, the use of specific compounds containing carbonate structural units as plasticizers in nail varnish compositions is provided by this invention.

BACKGROUND OF THE INVENTION

Cosmetic formulations have to have a number of properties in order to be suitable as nail varnishes. In this connection, it is particularly important that skin and nails are not irritated, the formulation can be applied easily, homogeneous and shiny films are formed upon application and these dry rapidly. Moreover, the film must adhere well to the nail surface, be as flexible as possible, and have good impact resistance and good wear resistance in order to prevent cracking and chipping of the nail varnish. For this, it is necessary for the cosmetic formulation to be able to form a hard but also flexible film. Also advantageous is a good resistance of the hardened film towards water in order to avoid detachment from the nail upon contact with water, for example during handwashing or washing up.

In this connection, plasticizers in nail varnish formulations improve the flexibility of the films and also influence other important parameters such as the shine, the drying time and the adhesion to the nails. For a long time, phthalates, such as dibutyl phthalate or camphor, or polymeric condensation products of formaldehyde or other aldehydes have been used virtually exclusively as plasticizers in nail varnish formulations. However, since these substances have proven to be injurious to health, there is a desire to replace these in nail varnish formulations.

U.S. Pat. No. 5,227,155 mentions for the first time the use of acetyl tributyl citrate (ATC) as plasticizer in nail varnish formulations. This substance has nowadays already to a large extent replaced the aforementioned health-injurious plasticizers. However, ATC leads to considerably reduced shine compared to the plasticizers used previously. Moreover, on account of its low molecular mass, ATC has a tendency to migrate out of the nail varnish film and deposit itself on the surface of the film. As a result, the surface of the film looks dull and the plasticizer effect in the nail varnish itself is lost. Moreover, nail varnish formulations with ATC as plasticizer harden only slowly.

WO 03/094870 A mentions, inter alia, propylene carbonate as a potential plasticizer for nail varnish formulations. However, propylene carbonate in nail varnish formulations exhibits a significantly too slight plasticizer effect in order to be able to be used constructively and efficiently. Moreover, propylene carbonate is volatile and can migrate out of the nail varnish film.

US 2010/0158835 A1 describes specific low molecular weight carbonates, such as, for example, glycerol carbonate, as plasticizers for nail varnish formulations. However, it is known for these plasticizers that the hardened nail varnish has poor resistance towards water. This is evident from a swelling or disintegration of the nail varnish and a reduced adhesion of the nail varnish on the nail. Moreover, nail varnish formulations with glycerol carbonate as plasticizer harden somewhat too slowly.

There was therefore a need for nail varnish compositions which comprise plasticizers which do not exhibit toxicologically unacceptable properties, are nonvolatile and, moreover, have only a slight ability to migrate from the film or through tissue and skin. Moreover, the nail varnish compositions should harden rapidly and have good water resistance.

DETAILED DESCRIPTION OF THE INVENTION

It was therefore an object of the present invention to provide a nail varnish composition which hardens quickly, has good water resistance and is based on plasticizers which are toxicologically acceptable and nonvolatile, and also have a low migratability. This object was achieved by a nail varnish composition comprising a plasticizer A) and a film former B), characterized in that the plasticizer A) has at least two carbonate structural units of the formula (I), a number-average molecular weight of ≥450 g/mol, determined by gel permeation chromatography (GPC) against polystyrene standards in tetrahydrofuran at 23° C. in accordance with DIN 55672-1, and a hydroxyl functionality of ≥1.5 and ≤6.

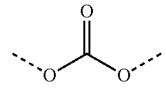

Formula (I)

In the context of this application, the number-average molecular weight is always determined by gel permeation chromatography (GPC) against polystyrene standard in tetrahydrofuran at 23° C. The procedure here is in accordance with DIN 55672-1: "Gel permeation chromatography, Part 1—Tetrahydrofuran as eluent" (SECurity GPC-System from PSS Polymer Service, flow rate 1.0 ml/min; columns: 2×PSS SDV linear M, 8×300 mm, 5 μm; RID detector). Here, polystyrene samples of known molar mass are used for the calibration. The calculation of the number-average molecular weight takes place with software assistantce. Baseline points and evaluation limits are stipulated according to DIN 55672 Part 1.

Surprisingly, it has now been found that polymeric compounds comprising at least two carbonate structural units are exceptionally suitable as plasticizers for nail varnish compositions. These compounds offer the advantage that they are nonvolatile and toxicologically acceptable. Moreover, on account of their polymeric structure, they have only a slight ability to migrate out from the nail varnish film or through tissue and skin. Moreover, the nail varnish compositions according to the invention harden quickly and have a particularly good water resistance.

In the context according to the invention, plasticizers are understood as meaning substances which make the films formed from a nail varnish formulation softer, more flexible, more supple and more elastic. It is exclusively a so-called external softening, which means that the plasticizer molecules are not covalently bonded onto other molecules present in the nail varnish formulation, in particular polymers, or bonded during film formation or hardening.

The invention further provides the use of compounds which have at least two carbonate structural units of the formula (I), a number-average molecular weight of ≥450 g/mol, determined by gel permeation chromatography (GPC) against polystyrene standard in tetrahydrofuran at 23° C. in accordance with DIN 55672-1, and a hydroxyl functionality of ≥1.5 and ≤6, as plasticizers in nail varnish compositions.

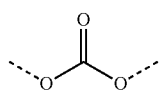

Formula (I)

The number-average molecular weight here is determined as has already been described above.

For the nail varnish compositions specified in this context and compounds suitable as plasticizers, the statements made relating to the nail varnish formulations according to the invention and the plasticizers A) used therein are applicable.

Preferably, the plasticizer A) does not enter into a chemical reaction with other components of the nail varnish composition. The plasticizer A) is thus preferably present in the composition and in the formed and/or hardened nail varnish film in chemically unchanged form. The plasticizer A) is or will therefore preferably not be covalently bonded to other molecules present in the nail varnish composition, in particular polymers.

The composition according to the invention comprises a plasticizer A) which has at least two, preferably at least three and particularly preferably at least four carbonate structural units of the formula (I).

The plasticizer A) used according to the invention has a number-average molecular weight of ≥450 g/mol, preferably of ≥450 g/mol and ≤6000 g/mol, particularly preferably of ≥500 g/mol and ≤5000 g/mol and very particularly preferably of ≥600 g/mol and ≤3000 g/mol.

The plasticizer A) furthermore comprises hydroxyl groups. Here, it has a hydroxyl functionality of ≥1.5 and ≤6, preferably of ≥1.8 and ≤3 and particularly preferably of ≥1.9 and ≤2.1.

Hydroxyl functionality is to be understood here as meaning the average number of hydroxyl groups per molecule, i.e. the number of terminal hydroxyl groups/number of molecules.

The hydroxyl groups are preferably present in free form in the composition and do not enter into a chemical reaction with other components of the composition.

Preferably, the plasticizer A) has no urethane and/or urea groups. Likewise preferably, the plasticizer A) has no aromatic structural units.

Preferably, the plasticizer A) is selected from polycarbonate polyols, polyester carbonate polyols and/or polyethercarbonate polyols or mixtures thereof, particularly preferably from polycarbonate polyols and/or polyester carbonate polyols and very particularly preferably the plasticizer A) is a polyester carbonate polyol. In a preferred embodiment of the invention, it is aliphatic polycarbonate polyols, polyester carbonate polyols and/or polyethercarbonate polyols which do not have any aromatic structural units, particularly preferably aliphatic polycarbonate polyols and/or polyester carbonate polyols and very particularly preferably aliphatic polyester carbonate polyols.

Very particularly preferably, the plasticizer A) is polycarbonate polyols and/or polyester carbonate polyols with a hydroxyl functionality of ≥1.9 and ≤2.1 and a number-average molecular weight of ≥600 g/mol and ≤3000 g/mol.

Polycarbonate polyols that can be used according to the invention are obtainable, for example, by reaction of carbonic acid derivatives, such as diphenyl carbonate, dimethyl carbonate or phosgene, with polyols, preferably diols. Suitable diols of this type are, for example, ethylene glycol, 1,2- and 1,3-propanediol, 1,3- and 1,4-butanediol, 1,6-hexanediol, 1,8-octanediol, neopentyl glycol, 1,4-bishydroxymethylcyclohexane, 2-methyl-1,3-propanediol, 2,2,4-trimethylpentane-1,3-diol, bisphenol A and tetrabromobisphenol A, and mixtures thereof.

Preferably, the diol component comprises 40 to 100% by weight of hexanediol, preferably 1,6-hexanediol and/or hexanediol derivatives. Preference is given to those polycarbonate polyols based on 1,6-hexanediol, particularly preferably those based on mixtures of 1,6-hexanediol and 1,4-butanediol.

Examples of suitable polycarbonate polyols are the products from Bayer Material Science AG obtainable under the tradenames Desmophen® C 2100, Desmophen® C 2200, Desmophen® C XP 2613, Desmophen® C 3100 XP, Desmophen® C 3200 XP and Desmophen® C XP 2716.

Polycarbonate polyols suitable according to the invention are also those which additionally comprise ester groups besides carbonate structures and are therefore also referred to as polyester carbonate polyols. These are in particular the polyester carbonate polyols known per se, as can be obtained, for example, according to the teaching of DE 1 770 245 A by reaction of di- or polyhydric alcohols with lactones, such as in particular ε-caprolactone, and subsequent reaction of the resulting polyesterdiols with carbonic acid derivatives, such as diphenyl carbonate, dimethyl carbonate or phosgene. Preferably, to produce the polyesterdiols, 1,6-hexanediol is reacted with caprolactones, in particular ε-caprolactone.

Examples of such suitable polyester carbonate polyols are the products from Bayer Material Science AG obtainable under the tradenames Desmophen® C 1100 or Desmophen® C 1200.

Likewise of suitability are polyethercarbonate polyols which additionally comprise ether groups besides carbonate structures. These are in particular the polyethercarbonate polyols known per se, as are obtainable, for example, in accordance with the process of EP 2 046 861 A by catalytic reaction of alkylene oxides (epoxides) and carbon dioxide in the presence of H-functional starter substances. Polyethercarbonate polyols can likewise be obtained by reaction of carbonic acid derivatives, such as diphenyl carbonate, dimethyl carbonate or phosgene, with polyols containing ether groups, preferably diols. Suitable diols are, for example, di-, tri- or tetraethylene glycol, dipropylene glycol, polypropylene glycols, dibutylene glycol, polybutylene glycols and polytetramethylene ether glycols, and mixtures thereof. Furthermore, as is known from DE 2 650 533 A, to produce the polyethercarbonate polyols, polyalkylene oxide polyols, in particular polyalkylene oxide diols, are preferably used as alcohols. Furthermore preferably used are also those diols which have been obtained by etherification of 1,6-hexanediol with other diols, in particular with themselves to give di- or trihexylene glycol. The preparation of such polyethercarbonate polyols is known, for example, from EP 0 292 772 A.

The polycarbonate polyols, polyester carbonate polyols and/or polyether carbonate polyols are preferably essentially linear. However, they may optionally be lightly branched as a result of the incorporation of polyfunctional components with an OH functionality >2, in particular low molecular weight polyols. Of suitability for this purpose are, for example, glycerol, trimethylolpropane, hexanetriol-1,2,6, butanetriol-1,2,4, trimethylolpropane, pentaerythritol, quinitol, mannitol, sorbitol, methyl glycoside or 1,3,4,6-dianhydrohexites. Essentially linear means here that preferably 0 to 10 mol % of the alcohol building block with an OH functionality >2 are used for the preparation of A), particularly preferably 0 to 3 mol % and very particularly preferably no building blocks at all with an OH functionality >2.

The fraction of the plasticizer A) is preferably ≥0.1 and ≤20% by weight, particularly preferably ≥0.5 and ≤15% by weight and very particularly preferably ≥1 and ≤10% by weight, of the overall nail varnish formulation.

In a preferred embodiment of the invention, the nail varnish composition comprises no compounds which comprise isocyanate groups.

The composition according to the invention comprises, as further component, a film former B), which is preferably a film-forming polymer. This film former B) can also be referred to as primary film former B). Preferably, it is a cosmetic film former.

The primary film-forming polymer is advantageously selected from nitrocelluloses, cellulose acetobutyrates, cellulose acetopropionates, cellulose ethers and/or mixtures thereof. Particular preference is given to nitrocelluloses. Very particular preference is given to the nitrocelluloses with a nitrogen content between 11.2 and 12.8% commercially available under the RS grade. Within the RS grade, there are subtypes which differ in particular by virtue of their molecular weight. Furthermore, preference is given to using nitrocellulose RS ⅛ sec., nitrocellulose ¼ sec., nitrocellulose RS ½ sec., nitrocellulose RS 5-6 sec. and nitrocellulose 60-80 sec. in the composition according to the invention. These nitrocellulose are known under European nomenclature as nitrocellulose E 23 to nitrocellulose E 130.

The fraction of the film former B) in the composition according to the invention is preferably ≥5 and ≤30% by weight, particularly preferably ≥6 and ≤25% by weight and very particularly preferably ≥8 to ≤20% by weight, based on the total weight of the composition.

In a preferred embodiment of the invention, the composition comprises at least one further film former D) different from B), it being particularly preferably a film-forming polymer. This film former D) can also be referred to as a secondary film former D).

As secondary film formers D), preference is given to using polymers containing ester groups, particularly preferably polyester polyols.

The preferably used polyester polyols are the polycondensates, known per se, of di- and optionally tri- and tetraols and di- and optionally tri- and tetracarboxylic acids or hydroxycarboxylic acids or lactones. Instead of the free polycarboxylic acids, the corresponding polycarboxylic anhydrides or corresponding polycarboxylic acid esters of lower alcohols can also be used for preparing the polyesters.

Examples of suitable diols are ethylene glycol, butylene glycol, diethylene glycol, triethylene glycol, polyalkylene glycols such as polyethylene glycol, also 1,2-propanediol, 1,3-propanediol, 1,3-butanediol, 1,4-butanediol, 1,6-hexanediol and isomers, neopentyl glycol or hydroxypivalic acid neopentyl glycol ester, with 1,6-hexanediol and isomers, 1,4-butanediol, neopentyl glycol and hydroxypivalic acid neopentyl glycol ester being preferred. In addition, it is also possible to use polyols such as trimethylolpropane, glycerol, erythritol, pentaerythritol, trimethylolbenzene or trishydroxyethyl isocyanurate.

Dicarboxylic acids that can be used are phthalic acid, isophthalic acid, terephthalic acid, tetrahydrophthalic acid, hexahydrophthalic acid, cyclohexanedicarboxylic acid, adipic acid, azelaic acid, sebacic acid, glutaric acid, tetrachlorophthalic acid, maleic acid, fumaric acid, itaconic acid, malonic acid, suberic acid, 2-methylsuccinic acid, 3,3-diethylglutaric acid and/or 2,2-dimethylsuccinic acid. The corresponding anhydrides can also be used as acid source.

Additionally, monocarboxylic acids, such as benzoic acid and hexanecarboxylic acid, can also be co-used.

Preferred acids are aliphatic or aromatic acids of the type specified above. Particular preference is given to adipic acid, isophthalic acid and phthalic acid.

Hydroxycarboxylic acids which can be co-used as reaction participants in the preparation of a polyester polyol with terminal hydroxyl groups are, for example, hydroxycaproic acid, hydroxybutyric acid, hydroxydecanoic acid, hydroxystearic acid and the like. Suitable lactones are caprolactone, butyrolactone and homologs. Preference is given to caprolactone.

Polyesterpolyols can be used with a number-average molecular weight of preferably ≥450 and ≤6000 g/mol, particularly preferably ≥500 and ≤5000 g/mol and especially preferably ≥600 and ≤3000 g/mol. The number-average molecular weight is determined by means of GPC in tetrahydrofuran at 23° C. in accordance with the statements made above.

The polyesterpolyols are advantageously the products obtainable from Bayer Material Science AG under the following trade names, or mixtures thereof:

Desmophen® 1700, Desmophen® 1652, Desmophen® VPLS 2328, Desmophen® 850, Desmophen® 1150, Desmophen® 1155, Desmophen® 1145, Desmophen® 1800, Desmophen® 670, Desmophen® 1200, Desmophen® VPLS 2068, Desmophen® 1100, Desmophen® 2400 S, Desmophen® 2450 X, Desmophen® 800, Desmophen® VPLS 2249/1, Desmophen® 690 MPA, Desmophen® T 1665 SN/IB, Desmophen® 680 X, Desmophen® T1775 SN, Desmophen® 680 BA, Desmophen® T 2082, Desmophen® T XP 2374, Desmophen® 670 BA, Desmophen® VP LS 2388, Desmophen® 650 MPA, Desmophen®651 MPA, Desmophen® 651 MPA/X, Desmophen® 800 BA, Desmophen® 800 MPA, Desmophen® PL 800, Desmophen® PL 300 X, Desmophen® 1300 BA, Desmophen® 1300 EA, Desmophen® 1300 X, Desmophen® 1400 PR, Desmophen® PL 817, Desmophen® 1388 71 EA, Baycoll® AD 2055, Baycoll® AD 2047, Baycoll® AD 1225, Baycoll® AD 5027, Baycoll® AS 2060, Baycoll® AV 2113

Desmophen® 680 BA is used particularly advantageously.

Further advantageous secondary film formers which can be used in addition to or instead of the aforementioned polyesterpolyols are:

tosylamide/formaldehyde resins (such as, for example, Ketjenflex® MH and Ketjenflex® MS-80 from Akzo Nobel, Sulfonex® from Estron, Santolite MHP, Santolite MS 80 from FACONNIER or RESIMPOL 80 from PAN AMERICANA)

tosylamide/epoxy resins (such as, for example, Lustrabrite S, Lustrabrite S-70, Nagellite 3050 from Telechemische or Polytex® Resin, Polytex® NX-55 from Estron)

adipic acid/neopentyl glycol/phthalic anhydride copolymers (such as, for example, Uniplex 670-P from Unitex Chempol Corporation)

phthalic anhydride/glycerol/glycidyl decanoate copolymers phthalic anhydride/phthalic anhydride/glycol copolymers (such as, for example, Polynex Resin, 7809 Polynex Resin from Estron)

glycerol/phthalic acid copolymers styrene/acrylate/acrylonitrile copolymers polymers and copolymers of acrylates (such as, for example, ACRYLOID B66 from Dow)

copolymers of acrylates and styrene sucrose acetate isobutyrate (such as, for example, Eastman SAIB from Eastman Chemical company)

polyvinylbutyral resins alkyd resins (such as, for example, BECKOSOL ODE 230-70-E from DAINTPPON)

polyurethane resins (such as, for example, TRIXENE PR 4127 from Baxenden Chemicals Ltd.)

The quantitative fraction of the secondary film former D) in the composition according to the invention is preferably ≥0 and ≤30% by weight, particularly preferably ≥0.5 and ≤20% by weight and very particularly preferably ≥1 and ≤15% by weight, based on the total weight of the composition.

Furthermore preferably, the fraction of the sum of film former B) and D) is preferably ≥5 and ≤60% by weight, particularly preferably ≥10.5 and ≤45% by weight and very particularly preferably ≥11 and ≤35% by weight, based on the total nail varnish formulation.

In a further embodiment of the invention, the composition comprises at least one further plasticizer C) different from A).

The plasticizers C) used are advantageously plasticizers and/or plasticizing resins with a number-average molecular weight of less than 1500 g/mol in order to achieve the desired mechanical properties. Suitable plasticizers C) are, for example, glycols and esters and ethers thereof, esters of acids, in particular carboxylic acids, such as citrates, adipates, carbonates, tartrates, phosphates or sebacates, ethoxylated derivatives such as ethoxylated oils and/or mixtures thereof. For example, suitable plasticizers are diethylene glycol ethyl ether, diethylene glycol methyl ether, diethylene glycol n-butyl ether or diethylene glycol hexyl ether, ethylene glycol ethyl ether, ethylene glycol butyl ether, ethylene glycol hexyl ether, propylene glycol phenyl ether, propylene glycol diacetate, dipropylene glycol ethyl ether, tripropylene glycol methyl ether, diethylene glycol methyl ether, propylene glycol butyl diglycol solution, dibutyl phosphate, tributoxyethyl phosphate, tricresyl phosphate, triphenyl phosphate, glyceryl triacetate, butyl stearate, glycolic acid butyl ester, benzyl benzoate, butyl acetyl tricinoleate, glyceryl aceryl tricinoleate dibutyl phthalate, diisobutyl phthalate, dioctyl phthalate, dimethoxyethyl phthalate, diethyl phthalate, diamyl phthalate, triethyl citrate, tributyl citrate, tributyl acetylcitrate, triethyl acetylcitrate, tri(2-ethylhexyl) acetyl-, dibutyltartrate, triacetin, camphor, trimethylpentanyl diisobutyrate, triethylhexanoins, sucrose benzoate, dibutyl adipate, diisobutyl adipate, adipic acid diisopropyl ester, dipropylene glycol dibenzoate and/or mixtures thereof.

Certain resins with a low molecular weight can likewise be used as plasticizers C) and are considered to be external plasticizers since they plasticize the systems without dissolving the cellulose-containing film former resins. Advantageous plasticizers C) to be mentioned are adipate polyester, sebacate polyester or butyl acrylate resins.

The quantitative fraction of further plasticizers C) in the composition according to the invention is preferably in the range from ≥0 and ≤25% by weight, particularly preferably ≥0.5 and ≤15% by weight and very particularly preferably ≥1 and ≤5% by weight, based on the total weight of the composition.

Furthermore preferably, the fraction of the sum of plasticizers A) and C) is preferably ≥0.1 and ≤30% by weight, particularly preferably ≥2 and ≤20% by weight and very particularly preferably ≥3 and ≤12% by weight, based on the total nail varnish formulation.

In a preferred embodiment of the invention, both plasticizers A) and also plasticizers C) are used. The weight ratio of plasticizer A) to plasticizers C) here is preferably between 10:1 and 1:5, particularly preferably between 3:1 and 1:1.

In a further preferred embodiment, no further plasticizer is present in the composition alongside A).

The nail varnish composition according to the invention preferably further comprises a physiologically acceptable medium E). Consequently, components A) and B) and optionally C) and D) are present in the composition according to the invention preferably in the physiologically acceptable medium E), these components are particularly preferably exclusively present in the physiologically acceptable medium E).

Physiologically acceptable media are to be understood here as meaning substances which are toxicologically acceptable and are suitable for application to the human body, specifically to keratin-based body constituents such as nails.

Preferably, the physiologically acceptable medium E) of the composition according to the invention comprises an organic solvent or a mixture of organic solvents, particularly preferably it consists thereof. The preferred organic solvents are, for example:

ketones which are liquid at room temperature, such as, for example, methyl ethyl ketone, methyl isobutyl ketone, diisobutyl ketone, isophorone, cyclohexanone, acetone;

alcohols which are liquid at room temperature, such as, for example, ethanol, butanol, propanol, isopropanol, diacetone alcohol, 2-butoxyethanol, cyclohexanol;

propylene glycols which are liquid at room temperature, such as, for example, propylene glycol monomethyl ether, propylene glycol monomethyl ether acetate, dipropylene glycol mono-n-butyl ether;

cyclic ethers, such as, for example, γ-butyrolactone;

short-chain esters having 3 to 8 hydrocarbon atoms, such as, for example, ethyl acetate, methyl acetate, propyl acetate, isopropyl acetate, n-butyl acetate, isopentyl acetate, methoxypropyl acetate, t-butyl acetate, butyl acetate;

ethers which are liquid at room temperature, such as, for example, diethyl ether, dimethyl ether, dichlorodiethyl ether;

alkanes which are liquid at room temperature, such as, for example, decane, heptane, dodecane, hexane, cyclohexane;

glycols, such as, for example, ethylene glycol, propylene glycol, pentylene glycol, glycerol;

alkyl sulfoxides, such as, for example, dimethyl sulfoxide;

aldehydes which are liquid at room temperature, such as, for example, benzaldehyde, acetaldehyde;

3-ethylethoxypropionate;

carbonates, such as, for example, propylene carbonate, dimethyl carbonate;

acetals, such as, for example, methylal;

and mixtures of the specified solvents.

Particularly advantageously, the organic solvents are selected from the group of ethyl acetate, butyl acetate, propyl acetate, isobutyl acetate, ethanol, propanol, isopropanol, butanol, methyl ethyl ketone, methyl isobutyl ketone, heptane and/or hexane and mixtures thereof.

In the case of the composition according to the invention, the solvent fraction can be in the range from ≥10 and ≤95% by weight, preferably in the range from ≥15 and ≤80% by weight, and particularly preferably in the range from ≥20 and ≤70% by weight, based on the total weight of the composition.

In a further embodiment of the invention, the physiologically acceptable medium E) of the composition according to the invention comprises water and optionally a physiologically compatible, water-miscible organic solvent, such as, for example, aliphatic C1-C5 monoalcohols and C2-C8 glycols. The water used in the composition according to the invention can be flower water, pure demineralized water, mineral water, thermal water and/or seawater.

The quantitative fraction of the sum of water and of the optionally present physiologically compatible, water-miscible organic solvent in the composition according to the invention can be, for example, in the range from ≥10 and ≤90% by weight, preferably in the range from ≥15 and ≤80% by weight, and particularly preferably in the range from ≥20 and ≤70% by weight, based on the total weight of the composition.

However, the composition according to the invention particularly preferably comprises ≤5% by weight of water, based on the total weight of the composition.

Furthermore, the composition according to the invention can also comprise additives such as effect-imparting constituents, for example dyes or pigments, antioxidants, light protection agents, wetting agents, emulsifiers, dispersants, stabilizers, antifoams, fillers, flow-control agents, coalescing agents, preservatives, moisturizing substances, perfume, free-radical scavengers, thickeners, neutralizing agents, oils, waxes, fillers and active ingredients. Depending on the desired property profile and intended use of the composition according to the invention, up to 90% by weight, based on the total dry substance, of these additives (based on the sum of all additives) may be present in the end product. Total dry substance is to be understood here as meaning all nonvolatile fractions of the nail varnish composition.

The composition according to the invention can comprise an effect-imparting constituent. The specified constituent can be in particular color-imparting, but also provide other different effects, such as glitter and/or metallic effects. Preferably, the composition according to the invention comprises at least one dye, which is preferably selected from the group of lipophilic dyes, hydrophilic dyes, pigments, paillettes and mother of pearl. Particularly advantageously according to the invention, the fraction of the effect-imparting constituents is ≥0 and ≤50% by weight, particularly advantageously ≥0.5 and ≤30% by weight, very particularly advantageously from ≥1 and ≤15% by weight, in each case based on the total weight of the composition.

For example, lipophilic dyes can be used, such as Sudan I (yellow), Sudan II (orange), Sudan III (red), Sudan IV (scarlet), DC Red 17, DC Green 6, β-carotene, soya oil, DC Yellow 11, DC Violet 2, DC Orange 5 and DC Yellow 10.

Suitable pigments are in principle all inorganic or organic pigments which are used in cosmetic or dermatological composition. The pigments used according to the invention can be, for example, white or colored, and they may be encased or coated with a hydrophobic treatment composition or be uncoated.

Advantageously, the pigments are selected from the group of metal oxides, such as, for example, iron oxides (in particular the oxides that are yellow, red, brown or black in color), titanium dioxide, zinc oxide, cerium oxide, zirconium oxide, chromium oxide; manganese violet, ultramarine blue, Prussian blue, ultramarine and iron blue, bismuth oxide chloride, mother of pearl, mica pigments coated with titanium or bismuth oxide chloride, colored pearlescent pigments, for example titanium-mica pigments with iron oxides, titanium-mica pigments, in particular with iron blue or chromium oxide, titanium-mica pigments with an organic pigment of the aforementioned type, and pearlescent pigments based on bismuth oxide chloride, carbon black, the pigments of the D & C type, such as D&C Red No 5, 6, 7, 10, 11, 12, 13, 34, D&C Yellow Lake No 5 and D&C Red Lake No 2 and the coating materials based on cochineal red, barium, strontium, calcium and aluminum, and mixtures thereof.

To adjust the rheological properties, thickeners can be used as additives. Particularly advantageously according to the invention, the concentration of thickeners is ≥0 and ≤20% by weight, particularly advantageously ≥0.5 and ≤15% by weight, very particularly advantageously from ≥1 and ≤10% by weight, in each case based on the total weight of the composition.

Advantageous thickeners are organomodified clays, such as organomodified bentonites, stearalkonium bentonite, organomodified hectorites, stearalkonium hectorite, or organomodified montmorillonites, hydrophobic fumed silica, where the silanol groups have been substituted for trimethylsiloxy groups (AEROSIL® R812 from Evonik) or for dimethylsiloxy groups or polydimethylsiloxane (AEROSIL® R972, AEROSIL® R974 from Evonik, CAB-O-SIL® TS-530, CAB-O-SIL® TS-610, "CAB-O-SIL® TS-720 from Cabot), polysaccharide alkyl ethers (as described in EP 898958-A).

Particularly advantageously, the organomodified clays are selected from the group of quaternium-18 bentonites (Bentone® 3, Bentone® 38, Bentone® 38V from Elementis, Tixogel VP Claytone 40, Claytone SO from Southern Clay), stearalkonium bentonite (Bentone®27V from Elementis, Tixogel LG, Claytone AF from Southern Clay), quaternium-18/benzalkonium bentonite (Claytone HT from Southern Clay).

The compositions according to the invention can comprise fillers. Fillers are to be understood as meaning colorless or white, mineral or synthetic lamellar spherical or oblong inert particles that are insoluble in the physiologically acceptable medium of the composition according to the invention and which, for example, modify the rheological properties and the texture of the composition.

The fillers can be present in the composition according to the invention in, for example, an amount of ≥0 and ≤50% by weight and preferably from ≥0.5 to ≤30% by weight, based on the total weight of the composition.

Advantageous particulate fillers in the context of the present invention are talc, mica, silicon dioxide, kaolin, starch and derivatives thereof (for example tapioca starch, distarch phosphate, aluminum starch or sodium starch octenylsuccinate and the like), fumed silica, pigments which have neither primarily a UV filter effect nor a coloring effect (such as e.g. boron nitride etc.), boron nitride, calcium carbonate, dicalcium phosphate, magnesium carbonate, magnesium hydrogencarbonate, hydroxyapatites, microcrystalline cellulose, powders of synthetic polymers, such as polyamides (for example the polymers obtainable under the trade name "Nylon®"), polyethylene, poly-β-alanine, polytetrafluoroethylene ("Teflon®"), polyacrylate, polyurethane, lauroyllysines, silicone resin (for example the polymers obtainable under the trade name "Tospearl®" from Momentive Performance Materials), hollow particles of polyvinylidene/acrylonitriles (Expancel® from Akzo Nobel) or hollow particles of silicon oxide (Silica Beads® from MAPRECOS).

It is also an advantage of the composition according to the invention that fingernail care additives can be incorporated. Of suitability are, for example, vitamins B5, E and C and derivatives thereof, and also dimethyloxobenzodioxasilanes, calcium chloride, calcium pantothenate, panthenol, proteins, ceramides, myrrh, plant extracts, amino acid oils, such as, for example, cysteine and salts and derivatives thereof, cysteine, glutathione, biotin, urea and dimethylurea, alpha-hydroxy acids, such as citric acid and ascorbic acid, UV protectants, such as benzophenone-1, benzophenone-3, benzyl salicylate, etocrylene, drometrizole, butyl methoxydibenzoylmethane, and hardening additives such as formaldehyde and hydrolysates formed from chitin and/or keratin. Antimycotic additives are also possible.

In a preferred embodiment of the invention, the nail varnish composition comprises a plasticizer A), a film former B), optionally at least one further plasticizer C) different from A), optionally at least one further film former D) different from B), a physiologically acceptable medium E) and optionally additives F).

In a particularly preferred embodiment of the invention, the nail varnish composition comprises a plasticizer A), a film former B), optionally at least one further plasticizer C) different from A), at least one further film former D) different from B), a physiologically acceptable medium E) and optionally additives F).

In a very particularly preferred embodiment of the invention, the nail varnish composition consists of a plasticizer A), a film former B), optionally at least one further plasticizer C) different from A), optionally at least one further film former D) different from B), a physiologically acceptable medium E) and optionally additives F).

In a furthermore preferred embodiment, the nail varnish composition comprises ≥0.1 and ≤20% by weight of the plasticizer A), ≥5 and ≤30% by weight of the film former B), ≥0 and ≤25% by weight of the plasticizer C), ≥0 and ≤30% by weight of the film former D), ≥10 and ≤95% by weight of the physiologically acceptable medium E) and ≥0 and ≤20% by weight of additives F), where the data refer in each case to the total weight of the nail varnish composition and the sum of the components A) to F) add up to 100% by weight.

Advantageously, the fraction of the sum of the film formers B) and D) is here preferably ≥5 and ≤60% by weight and the fraction of the sum of the plasticizers A) and C) is preferably ≥0.1 and ≤30% by weight, in each case based on the total nail varnish formulation.

In a furthermore particularly preferred embodiment, the nail varnish composition comprises ≥1 and ≤10% by weight of the plasticizer A), ≥10 and ≤20% by weight of the film former B), ≥1 and ≤5% by weight of the plasticizer C), ≥1 and ≤15% by weight of the film former D), ≥20 and ≤70% by weight of the physiologically acceptable medium E) and ≥0.5 and ≤10% by weight of additives F), where the data refer in each case to the total weight of the nail varnish composition and the sum of the components A) to F) adds up to 100% by weight.

Advantageously, the fraction of the sum of the film formers B) and D) here is preferably ≥11 and ≤35% by weight and the fraction of the sum of the plasticizers A) and C) is preferably ≥3 and ≤12% by weight, in each case based on the total nail varnish formulation.

The nail varnish compositions according to the invention may also be systems curable by UV radiation. However, they are preferably not UV-curable systems.

The nail varnish composition according to the invention is preferably dispensed into vessels with a capacity of ≤50 ml, preferably ≤20 ml.

The invention further provides a coating obtainable from a nail varnish composition according to the invention. This coating is to be understood in particular as meaning a film which is formed upon applying the nail varnish composition to a substrate and then hardens. In this connection, the hardening of the film can take place without auxiliaries, but also with the assistance of for example, a UV lamp.

The coating obtainable from the nail varnish formulation according to the invention preferably has a pendulum hardness of ≥20 könig/s and ≤50 könig/s, preferably ≥30 könig/s and ≤45 könig/s. The pendulum hardness is determined here as given in the method section of the examples.

Furthermore, the coating obtainable from the nail varnish formulation according to the invention preferably has a gloss of ≥70 and ≤99, particularly preferably of ≥90 and ≤98. The gloss is determined here in accordance with DIN 67530 by means of a "micro-haze plus" gloss meter from BYK Gardner GmbH, Germany, after drawdown (200 μm wet) and drying at 23° C. of the respective composition after 24 hours on a black/white Leneta card. The gloss is measured at an angle of 60°.

Furthermore, the coating obtainable from the nail varnish formulation according to the invention is preferably resistant to water, meaning in particular that the hardened coating film obtained, after 4 h in water at 40° C., is still complete, and particularly preferably the film is then still complete and also clear. The water resistance is determined here as given in the method section of the examples.

The invention likewise provides a substrate coated with a coating according to the invention. The substrate here is preferably keratin-based materials, in particular fingernails and toenails, but also artificial nails which have already been attached to the human body or are intended for attachment to the human body. Such artificial nails are based, for example, on materials such as synthetic plastics.

The invention further provides a cosmetic method for coating fingernails and/or toenails, in which a nail varnish composition according to the invention is applied to fingernails and/or toenails. Fingernails and toenails are to be understood here as also meaning artificial nails which have already been attached to the human body or are intended for attachment to the human body.

The nail varnish composition is applied to the fingernails and/or toenails with an aid. The aid is in particular a fine brush. After application, a film preferably forms on the nail. This film then preferably hardens. Preferably, the film hardens at 23° C. over the course of ≤430 s, particularly preferably within ≤410 s. The drying time is determined here as stated in the method section of the examples.

The present invention is illustrated by reference to the following examples.

EXAMPLES

Methods:

The pendulum hardnesses were determined on a König Pendulum Hardness Tester from BYK Gardner GmbH, Germany in accordance with DIN EN ISO 1522, after drawdown (240 µm wet) and drying of the respective composition overnight (16 hours) at 23° C. and 50% relative atmospheric humidity on a glass plate. In each case, the mean was formed from 3 measurements.

The drying time at room temperature was determined after application of the composition to a glass plate (120 µm wet) by means of a drying time recorder from BYK Gardner GmbH, Germany in accordance with ASTM D5895. The drying time "to the touch" was ascertained.

To measure the water resistance, glass plates were immersed, following application of the composition (240 µm) and drying for 24 hours at 23° C. and 50% relative atmospheric humidity, into a water bath at 40° C. for a period of 4 hours. The water resistance was determined qualitatively.

The fractions of the components are given in each case in % by weight and are always based on the amount of total composition.

Substances and Abbreviations Used:

Collodium: Mixture of 50% by weight of butyl acetate, 26% by weight of ethyl acetate and 24% by weight of nitrocellulose (the nitrocellulose used comprises 20% by weight of isopropanol).

Desmophen® C1100: Polyestercarbonate polyol with a number-average molar mass of 1000 g/mol and an OH functionality of 2; commercial product from Bayer MaterialScience AG (abbreviation: D C1100)

Desmophen® 670 BA: lightly branched, hydroxyl-group-containing polyesterpolyol with a hydroxyl content of approx. 3.5% (in accordance with DIN 53240/2) and a viscosity of approx. 2800 mPas (at 23° C., in accordance with DIN EN ISO 3219/A.3), dissolved in butyl acetate (the characteristic data refer to the solution with 80% nonvolatile fraction in accordance with DIN EN ISO 3251, measured at 125° C.), commercial product from Bayer MaterialScience AG (abbreviation: D 670 BA)

Desmophen® 800 BA: highly branched, hydroxyl-group-containing polyesterpolyol with a hydroxyl content of approx. 6.9% (in accordance with DIN 53240/2) and a viscosity of approx. 3500 mPas (at 23° C., in accordance with DIN EN ISO 3219/A.3), dissolved in butyl acetate (the characteristic data refer to the solution with 80% nonvolatile fraction in accordance with DIN EN ISO 3251, measured at 125° C.), commercial product from Bayer MaterialScience AG (abbreviation: D 800 BA)

Investigation of the Plasticizing Effect:

Nail varnish formulations based on collodium (film former 1), butyl acetate (physiologically acceptable medium) and various plasticizers (ATC, glycerol carbonate, propylene carbonate and Desmophen® C1100) were investigated as to their pendulum hardness. The lower the hardness of the film formed from the particular composition, the stronger the plasticizing effect of the substances used. Table 1 gives the results of these investigations. It is evident that propylene carbonate is unsuitable as plasticizer for nail varnish formulations and worse plasticizer effects are achieved with polyesterpolyols.

TABLE 1

| E | Collodium | ATC | Glycerol carbonate | Propylene carbonate | D C 1100 | Butyl acetate | D 680 BA | D 670 BA | D 800 BA | Pendulum hardness [König/s] |
|---|---|---|---|---|---|---|---|---|---|---|
| 1 | 50 | 10 | | | | 40 | | | | 7 |
| 2 | 50 | | 10 | | | 40 | | | | 7 |
| 3 | 50 | | | 10 | | 40 | | | | 208 |
| 4 | 50 | | | | 10 | 40 | | | | 7 |
| 5 | 50 | | | | | 40 | 10 | | | 88 |
| 6 | 50 | | | | | 40 | | 10 | | 224 |
| 7 | 50 | | | | | 40 | | | 10 | 73 |

Desmophen® 3100 XP: Polycarbonate polyol with a number-average molar mass of 1000 g/mol and an OH functionality of 2; commercial product from Bayer MaterialScience AG (abbreviation: D 3100 XP)

Desmophen® 680 BA: Branched, hydroxyl-group-containing polyesterpolyol with a hydroxyl content of approx. 2.2% (in accordance with DIN 53240/2) and a viscosity of approx. 3000 mPas (at 23° C., in accordance with DIN EN ISO 3219/A.3), dissolved in butyl acetate (the characteristic data refer to the solution with 70% nonvolatile fraction in accordance with DIN EN ISO 3251, measured at 125° C.) commercial product from Bayer MaterialScience AG (abbreviation: D 680 BA)

Investigation of Drying Time and Water Resistance:

Nail varnish formulations based on collodium (film former 1), Desmophen® 680 BA (film former 2), butyl acetate (physiologically acceptable medium) and various plasticizers (glycerol carbonate, Desmophen® C1100 and Desmophen® 3100 XP) were investigated as regards their drying time and water resistance. The formulations were in each case adjusted here such that they have a pendulum hardness between 35 and 45 König/s. Table 2 summarizes the compositions and the observed results. Surprisingly, it has been found that the films formed from the nail varnish compositions 6 and 7 according to the invention have both a somewhat improved drying time compared to the films from comparative experiment 5, as well as considerably better water resistance.

TABLE 2

| E | Collodium | D 680 BA | Glycerol carbonate | D C 1100 | D 3100 XP | Butyl acetate | Pendulum hardness [König/s] | Drying time [s] | Water resistance |
|---|---|---|---|---|---|---|---|---|---|
| 5* | 50 | 10 | 5 | | | 35 | 35 | 446 | Destroyed, milky film |
| 6 | 50 | 10 | | 6 | | 34 | 44 | 381 | Clear, complete film |
| 7 | 50 | 10 | | | 7 | 33 | 41 | 406 | Clear, complete film |

*Comparative experiment

The foregoing examples of the present invention are offered for the purpose of illustration and not limitation. It will be apparent to those skilled in the art that the embodiments described herein may be modified or revised in various ways without departing from the spirit and scope of the invention. The scope of the invention is to be measured by the appended claims.

Various aspects of the subject matter described herein are set out in the following numbered clauses:

1. A nail varnish composition comprising a plasticizer A) and a film former B), characterized in that the plasticizer A) has at least two carbonate structural units of the formula (I), a number-average molecular weight of ≥450 g/mol, determined by gel permeation chromatography against polystyrene standards in tetrahydrofuran at 23° C. in accordance with DIN 55672-1, and a hydroxyl functionality of ≥1.5 and ≤6.

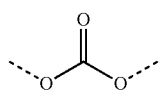

(I)

2. The nail varnish composition as recited in clause 1, characterized in that the plasticizer A) does not enter into a chemical reaction with other components of the nail varnish composition.
3. The nail varnish composition as recited in one of clauses 1 and 2, characterized in that the plasticizer A) has no urethane and/or urea groups.
4. The nail varnish composition as recited in one of clauses 1 to 3, characterized in that it comprises at least one further plasticizer C) different from A).
5. The nail varnish composition as recited in one of clauses 1 to 4, characterized in that the plasticizer A) has a hydroxyl functionality of ≥1.9 and ≤2.1.
6. The nail varnish composition as recited in one of clauses 1 to 5, characterized in that the plasticizer A) has a number-average molecular weight of ≥450 g/mol and ≤6000 g/mol.
7. The nail varnish composition as recited in one of clauses 1 to 6, characterized in that the plasticizer A) is selected from polycarbonate polyols, polyester carbonate polyols and/or polyethercarbonate polyols.
8. The nail varnish composition as recited in one of clauses 1 to 7, characterized in that the fraction of the plasticizer A) is ≥0.1 and ≤20% by weight of the total nail varnish formulation.
9. The nail varnish composition as recited in one of clauses 1 to 8, characterized in that the film former B) is selected from nitrocelluloses, cellulose acetobutyrates, cellulose acetopropionates, cellulose ethers and/or mixtures thereof.
10. The nail varnish composition as recited in one of clauses 1 to 9, characterized in that this comprises at least one further film former D) different from B).
11. The nail varnish composition as recited in clause 10, characterized in that D) is a polyesterpolyol.
12. A coating obtainable from a nail varnish composition as recited in one of clauses 1 to 11.
13. A substrate coated with a coating as recited in clause 12.
14. A cosmetic method for coating fingernails and/or toenails, in which a nail varnish composition as recited in one of clauses 1 to 11 is applied to fingernails and/or toenails.
15. The use of compounds which have at least two carbonate structural units of the formula (I),

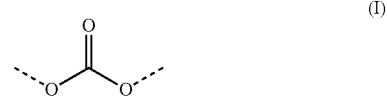

(I)

a number-average molecular weight of ≥450 g/mol, determined by gel permeation chromatography (GPC) against polystyrene standards in tetrahydrofuran at 23° C. in accordance with DIN 55672-1, and a hydroxyl functionality of ≥1.5 and ≤6, as plasticizers in nail varnish compositions.

The invention claimed is:
1. A nail varnish composition comprising a plasticizer A) and a film former B), wherein the plasticizer A) has at least two carbonate structural units of the formula (I),

(I)

a number-average molecular weight of ≥450 g/mol, determined by gel permeation chromatography against polystyrene standards in tetrahydrofuran at 23° C. in accordance with DIN 55672-1, and a hydroxyl functionality of ≥1.5 and ≤6 and wherein the plasticizer A) does not enter into a chemical reaction with other components of the nail varnish composition.
2. The nail varnish composition according to claim 1, wherein the plasticizer A) contains no urethane and/or urea groups.
3. The nail varnish composition according to claim 1, wherein that the composition further comprises at least one additional plasticizer C) different from A).
4. The nail varnish composition according to claim 1, wherein the plasticizer A) has a hydroxyl functionality of ≥1.9 and ≤2.1.
5. The nail varnish composition according to claim 1, wherein the plasticizer A) has a number-average molecular weight of ≥450 g/mol and ≤6000 g/mol.
6. The nail varnish composition according to claim 1, wherein the plasticizer A) is selected from the group consisting of polycarbonate polyols, polyester carbonate polyols and polyethercarbonate polyols.

7. The nail varnish composition according to claim 1, wherein the fraction of the plasticizer A) is ≥0.1 and ≤20% by weight of the total nail varnish formulation.

8. The nail varnish composition according to claim 1, wherein the film former B) is selected from the group consisting of nitrocelluloses, cellulose acetobutyrates, cellulose acetopropionates, cellulose ethers and mixtures thereof.

9. The nail varnish composition according to claim 1, wherein the composition further comprises at least one additional film former D) different from B).

10. The nail varnish composition according to claim 9, wherein D) is a polyesterpolyol.

11. A coating obtainable from a nail varnish composition according to claim 1.

12. A substrate coated with a coating according to claim 11.

13. A cosmetic method for coating fingernails and/or toenails, the method comprising applying a nail varnish composition according to claim 1 to fingernails and/or toenails.

\* \* \* \* \*